US00PP15006P2

(12) United States Plant Patent
Hooijman

(10) Patent No.: US PP15,006 P2
(45) Date of Patent: Jul. 13, 2004

(54) GYPSOPHILA PLANT NAMED 'ESMASIA'

(50) Latin Name: *Gypsophila hybrida*
Varietal Denomination: Esmasia

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 0 days.

(21) Appl. No.: 10/654,445

(22) Filed: Sep. 2, 2003

(51) Int. Cl.[7] ..... A01H 5/00
(52) U.S. Cl. ..... Plt./354
(58) Field of Search ..... Plt./354

*Primary Examiner*—Kent Bell
(74) *Attorney, Agent, or Firm*—C. A. Whealy

(57) ABSTRACT

A distinct cultivar of Gypsophila plant named 'Esmasia', characterized by its erect and strong flowering stems; freely flowering habit; white-colored flowers arranged in symmetrical compound cymes with many petals per flower; good post-production longevity; and resistance to Botrytis and Alternaria.

1 Drawing Sheet

Botanical classification/cultivar designation: *Gypsophila hybrida* cultivar Esmasia.

BACKGROUND OF THE INVENTION

The present Invention relates to a new and distinct cultivar of Gypsophila plant, botanically known as *Gypsophila hybrida*, grown commercially as a cut flower, and hereinafter referred to by the name 'Esmasia'.

The new Gypsophila is a product of a planned breeding program conducted by the Inventor in El Quinche, Pichincha, Ecuador. The objective of the program is to create new freely flowering Gypsophila cultivars with many petals per flower and straight stems.

The new Gypsophila originated from a cross-pollination made in January, 2000, in a controlled environment in El Quinche, Pichincha, Ecuador, of a proprietary Gypsophila selection identified as Line 33, not patented, as the female, or seed, parent with an unknown Gypsophila selection, not patented, as the male, or pollen, parent. The new Gypsophila was discovered and selected by the Inventor as a single flowering plant within the progeny of the stated cross-pollination grown in a controlled environment in El Quinche, Pichincha, Ecuador.

Asexual reproduction of the new Gypsophila by cuttings taken at El Quinche, Pichincha, Ecuador since July, 2000, has shown that the unique features of this new Gypsophila are stable are reproduced true to type in successive generations.

SUMMARY OF THE INVENTION

The following traits have been repeatedly observed and are determined to be the unique characteristics of 'Esmasia'. These characteristics in combination distinguish 'Esmasia' as a new and distinct cultivar:

1. Erect and strong flowering stems.
2. Freely flowering habit.
3. White-colored flowers arranged in symmetrical compound cymes with many petals per flower.
4. Good post-production longevity.
5. Resistant to Botrytis and Alternaria.

Plants of the new Gypsophila can be compared to plants of the female parent selection, Line 33. In side-by-side comparisons conducted in El Quinche, Pichincha, Ecuador, plants of the new Gypsophila differed from plants of the female parent selection in the following characteristics:

1. Flowering stems of plants of the new Gypsophila were stronger than flowering stems of plants of the female parent selection.
2. Plants of the new Gypsophila had larger flowers with more petals per flower than plants of the female parent selection.
3. Plants of the new Gypsophila flowered more uniformly than plants of the female parent selection.

Plants of the new Gypsophila can also be compared to plants of the cultivar Dangypflash, disclosed in U.S. Plant Pat. No. 12,422. In side-by-side comparisons conducted in El Quinche, Pichincha, Ecuador, plants of the new Gypsophila differed from plants of the cultivar Dangypflash in the following characteristics:

1. Flowering stems of plants of the new Gypsophila were more erect than flowering stems of plants of the cultivar Dangypflash.
2. Plants of the new Gypsophila had shorter leaves than plants of the cultivar Dangypflash.
3. Plants of the new Gypsophila had smaller flowers with more petals per flower than plants of the cultivar Dangypflash.
4. Plants of the new Gypsophila were more freely flowering than plants of the cultivar Dangypflash.

The cultivar Esmasia has not been observed under all possible environmental conditions. The phenotype may vary somewhat with variations in environments such as temperature and light intensity, without, however, any variance in genotype.

BRIEF DESCRIPTION OF THE PHOTOGRAPHS

The accompanying colored photographs illustrate the overall appearance of the new Gypsophila, showing the colors as true as it is reasonably possible to obtain in colored reproductions of this type. Colors in the photographs may differ slightly from the color values cited in the detailed botanical description which accurately describe the colors of the new Gypsophila.

The larger photograph comprises a side perspective view of a typical flowering stem of 'Esmasia' with developing flowers.

The inserted photograph is a close-up view of a typical inflorescence of 'Esmasia'.

DETAILED BOTANICAL DESCRIPTION

In the following description, color references are made to The Royal Horticultural Society Colour Chart, 2001 Edition, except where general terms of ordinary dictionary significance are used. The aforementioned photograph, following observations and measurements describe 18-week old plants grown in an outdoor nursery in El Quinche, Pichincha, Ecuador. During the production of the plants, day temperatures ranged from 11 to 28° C. and night temperatures ranged from 5 to 11° C. Plants were pinched about five weeks after planting.

Botanical classification: *Gypsophila hybrida* cultivar Esmasia.

Commercial classification: Cut flower Gypsophila.

Parentage:

*Female, or seed, parent.*—Proprietary *Gypsophila hybrida* selection identified as Line 33, not patented.

*Male, or pollen, parent.*—Unknown *Gypsophila hybrida* selection, not patented.

Propagation:

*Type.*—By cuttings.

*Time to initiate roots.*—About 16 to 21 days at a temperature of 17 to 25° C.

*Time to produce a rooted young plant.*—About 35 to 42 days at a temperature of 17 to 25° C.

*Root description.*—Fine, fibrous; developing roots, 158A; fully developed roots, 23D.

Plant description:

*Appearance.*—Perennial cut flower. Erect and strong flowering stems; inverted triangle form. Freely flowering; many-petalled white-colored flowers arranged in symmetrical and moderately dense compound cymes. Moderately vigorous growth habit.

*Branching habit.*—Freely branching; per plant, about 20 flowering stems produced per year.

*Plant height.*—About 98.5 cm.

*Plant width.*—About 40 cm.

*Flowering stem description.*—Length: About 93.5 cm. Diameter: About 4.5 mm. Internode length: About 6 cm. Strength: Moderately strong. Texture: Glabrescent. Color: 144A.

*Foliage description.*—Arrangement: Opposite, decussate, simple; sessile. Shape: Lanceolate. Apex: Acute. Base: Cuneate. Margin: Entire. Length: About 7.7 cm. Width: About 1.4 cm. Texture: Glabrous, smooth; waxy. Venation pattern: Parallel. Color: Developing and fully expanded leaves, upper surface: 137A to 137B. Developing and fully expanded leaves, lower surface: 137A to 137B. Venation, upper and lower surfaces: 138B.

Flowering description:

*Appearance.*—Symmetrical and hemispherical compound cymes with numerous many-petalled luminous white-colored flowers, flowers rotate. Very freely flowering, about 256 flowers per inflorescence. Flowers face mostly upright to slightly outwardly.

*Flowering response.*—In Ecuador, plants flower year round. Plants begin flowering about 12 to 13 weeks after pinching.

*Post-production longevity.*—As a cut flower, flowers last for about 12 to 14 days. Flowers persistent.

*Fragrance.*—Sweet, pleasant.

*Inflorescence height.*—About 11.5 cm.

*Inflorescence width.*—About 9.5 cm.

*Flower bud.*—Shape: Somewhat globose. Length: About 1.5 mm. Diameter: About 1.7 mm. Color: Towards the base, 155B; mid-section, 138B; towards the apex, 182A.

*Flower diameter.*—About 6 mm.

*Flower depth (height).*—About 5 mm.

*Petals/petaloids.*—Quantity per flower: About 77 arranged in about ten clusters; clusters fused at base. Shape: Oval to spatulate. Apex: Obtuse, blunt, retuse. Margin: Entire. Length: About 3 mm. Width: About 1 mm. Texture: Smooth, glabrous; waxy. Color: When opening, upper and lower surfaces: 155B; color becoming closer to 158B with development. Fully opened, upper and lower surfaces: 155B.

*Sepals.*—Quantity per flower: About five. Shape: Roughly elliptic. Apex: Acute. Base: Fused. Margin: Entire. Calyx length: About 3 mm. Calyx diameter: About 3 mm. Color, upper and lower surfaces: Towards the base, 155B; mid-section, 138B; towards the apex, 182A.

*Peduncle.*—Strength: Moderately strong. Length: About 3.5 cm. Diameter: About 1.3 mm. Angle: About 49° from vertical. Texture: Smooth. Color: 137C.

*Pedicels.*—Strength: Moderately strong. Length: About 5.3 mm. Diameter: About 0.4 mm. Angle: About 45° from vertical. Texture: Smooth. Color: 152A.

*Reproductive organs.*—Stamens: Quantity per flower: About two. Anther shape: Reniform to globose. Anther size: Diminutive. Anther color: 168D. Pollen: Scarce. Pollen color: 168D. Pistils: Quantity per flower: About two. Style length: Less than 1 mm. Style color: Close to 155B. Pistil length: Less than 1 mm. Stigma color: Close to 155B. Ovary color: 141C.

*Seed/fruit development.*—Seed and fruit development has not been observed.

Disease/pest resistance: Plants of the new Gypsophila have been observed to be resistant to Botrytis and Fusarium. Plants of the new Gypsophila have not been observed to be resistant to pests and other pathogens common to Gypsophilas.

It is claimed:

1. A new and distinct cultivar of Gypsophila plant named 'Esmasia', as illustrated and described.

* * * * *

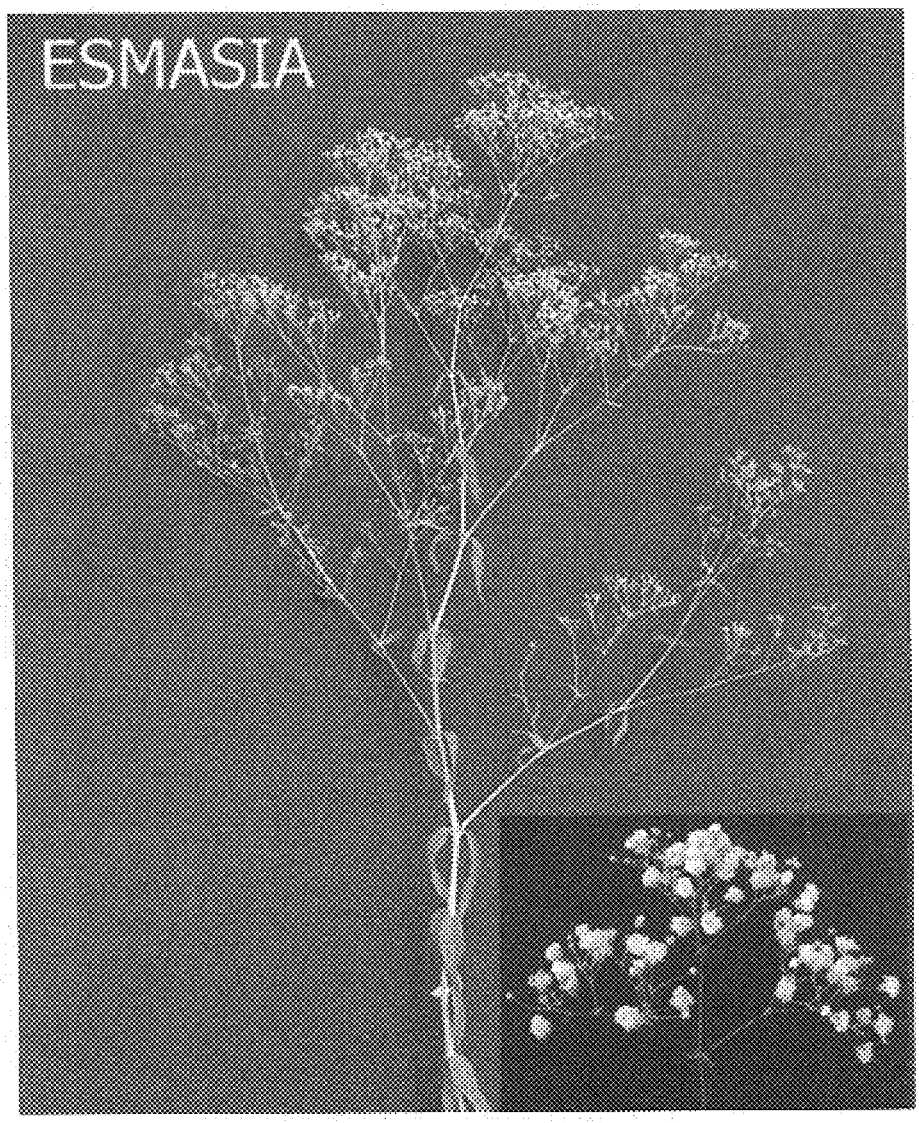
ESMASIA